United States Patent
Okabe

(10) Patent No.: US 9,616,081 B2
(45) Date of Patent: *Apr. 11, 2017

(54) ANTITUMOR AGENT INCLUDING LOW-DOSE IRINOTECAN HYDROCHLORIDE HYDRATE

(71) Applicant: TAIHO PHARMACEUTICAL CO., LTD., Chiyoda-ku (JP)

(72) Inventor: Hiroyuki Okabe, Hanno (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/779,759

(22) PCT Filed: Mar. 27, 2014

(86) PCT No.: PCT/JP2014/058733
§ 371 (c)(1),
(2) Date: Sep. 24, 2015

(87) PCT Pub. No.: WO2014/157444
PCT Pub. Date: Oct. 2, 2014

(65) Prior Publication Data
US 2016/0082031 A1 Mar. 24, 2016

(30) Foreign Application Priority Data

Mar. 27, 2013 (JP) ................. 2013-066074

(51) Int. Cl.
| | | |
|---|---|---|
| A61K 31/70 | (2006.01) | |
| A01N 43/04 | (2006.01) | |
| A61K 31/7072 | (2006.01) | |
| A61K 31/4745 | (2006.01) | |
| A61K 31/506 | (2006.01) | |
| A61K 31/513 | (2006.01) | |
| A61K 31/706 | (2006.01) | |
| A61K 31/7064 | (2006.01) | |
| A61K 31/7068 | (2006.01) | |

(52) U.S. Cl.
CPC ...... *A61K 31/7072* (2013.01); *A61K 31/4745* (2013.01); *A61K 31/506* (2013.01); *A61K 31/513* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | |
|---|---|---|
| 7,799,783 B2 | 9/2010 | Emura et al. |
| 2009/0053302 A1 | 2/2009 | Boulikas |
| 2010/0056463 A1 | 3/2010 | Raederstorff et al. |

FOREIGN PATENT DOCUMENTS

| | | |
|---|---|---|
| JP | 2009-528340 A | 8/2009 |
| JP | 2010-500964 A | 1/2010 |
| JP | 2011-157298 A | 8/2011 |
| WO | 2006/080327 A1 | 8/2006 |

OTHER PUBLICATIONS

Ishida et al. Mol Cancer Ther Nov. 2013 (12) (11 Supplement) B87; DOI: 10.1158/1535-7163.TARG-13-B87.*
Ayumu Goto, "Current Evidence of Irinotecan Combination Chemotherapy with TS-1 in Patients with Advanced Colorectal Cancer," Japan Journal of Cancer and Chemotherapy, vol. 33, No. 7, Jul. 2006, pp. 896-900 (with English abstract).
Sotaro Sadahiro, et al., "Two Patients with Recurrent Colon Cancer Who Underwent Surgery Following a Combination of Irinotecan and UFT," Japan Journal of Cancer and Chemotherapy, vol. 29, No. 11, Nov. 2002, pp. 2013-2018 (with English abstract).
K. Yamazaki, et al., "A first combination phase I study of TAS-102 and irinotecan (Iri) in Japanese patients (pts) with metastatic colorectal cancer (mCRC) refractory to fluoropyrimidine (FU) and oxaliplatin (Ox)," European Journal of Cancer, vol. 49, Suppl. 2, Sep. 2013 (3 pages).
Olaf H. Temmink, et al., "Therapeutic potential of the dual-targeted TAS-102 formulation in the treatment of gastrointestinal malignancies," Cancer Sci., vol. 98, No. 6, Jun. 2007, pp. 779-789.
Michael J. Overman, et al., "Phase 1 study of TAS-102 administered once daily on a 5-day-per-week schedule in patients with solid tumors," Invest New Drugs (2008), vol. 26, May 2008, pp. 445-454.
Takayuki Yoshino, et al., "TAS-102 monotherapy for pretreated metastatic colorectal cancer: a double-blind, randomized, placebo-controlled phase 2 trial," Lancet Oncology, vol. 13, Oct. 2012, pp. 993-1001.
Mace L. Rothenberg, "Irinotecan (CPT-11): Recent Developments and Future Directions—Colorectal Cancer and Beyond," The Oncologist, vol. 6(1), 2001, pp. 66-80.
Olaf H. Temmink, et al., "Irinotecan-induced cytotoxicity to colon cancer cells in vitro is stimulated by pre-incubation with trifluorothymidine," European Journal of Cancer, vol. 43, 2007, pp. 175-183.
International Search Report issued Jun. 17, 2014 in PCT/JP2014/058733 filed Mar. 27, 2014.
U.S. Appl. No. 14/780,269, filed Sep. 25, 2015, Okabe.

* cited by examiner

*Primary Examiner* — Patrick Lewis
(74) *Attorney, Agent, or Firm* — Oblon, McClelland, Maier & Neustadt, L.L.P.

(57) ABSTRACT

Provided is a novel combination therapy using an FTD/TPI combination drug which exhibits remarkable antitumor effects, and few side effects.

An antitumor agent is characterized in that the FTD/TPI combination drug is administered, using a reduced amount of trifluridine, at a dose in the range of 35 to 70 mg/m$^2$/day and CPT-11 is administered at a dose in the range of 45 to 144 mg/m$^2$/day.

20 Claims, 7 Drawing Sheets

ANTITUMOR AGENT INCLUDING LOW-DOSE IRINOTECAN HYDROCHLORIDE HYDRATE

TECHNICAL FIELD

The present invention relates to an antitumour agent using a trifluridine/tipiracil hydrochloride combination drug in combination with irinotecan hydrochloride hydrate, and to an agent for potentiating the antitumor effect of irinotecan hydrochloride hydrate.

BACKGROUND ART

Trifluridine (also called: α,α,α-trifluorothymidine. Hereinafter, also referred to as "FTD") exerts an antitumor effect due to an action for inhibiting thymidylate formation and an action for inhibiting DNA synthesis by incorporation into DNA. On the other hand, tipiracil hydrochloride (chemical name: 5-chloro-6-[(2-iminopyrrolidin-1-yl)methyl]-pyrimidine-2,4(1H,3H)-dione hydrochloride. Hereinafter, also referred to as "TPI") has an action for inhibiting thymidine phosphorylase. It is known that the antitumor effect of FTD is potentiated by the TPI suppressing the degradation of FTD in vivo caused by thymidine phosphorylase (Patent Literature 1). Currently, an antitumor agent containing FTD and TPI in a molar ratio of 1:0.5 (hereinafter referred to as "FTD/TPI combination drug") is under development as a therapeutic agent for solid cancers, for example, colorectal cancer (Non Patent Literatures 1 and 2).

Further, irinotecan hydrochloride hydrate (hereinafter, also referred to as "CPT-11") is a camptothecin derivative whose active metabolite is SN-38 and which suppresses the synthesis and transcription of DNA by inhibiting topoisomerase I, thereby to exert an antitumor effect. CPT-11 is clinically used as a therapeutic agent for a wide range of cancer types including, for example, small cell lung cancer, non-small cell lung cancer, cervical cancer, ovarian cancer, gastric cancer, colorectal cancer, breast cancer, squamous cell carcinoma, and malignant lymphoma (Non Patent Literature 3).

Further, when FTD and SN-38 were allowed to act on a colorectal cancer cell line, a synergistic cytotoxicity was observed and thus a combination therapy using an FTD/TPI combination drug and CPT-11 has been expected (Non Patent Literature 4).

CITATION LIST

Patent Literature

Patent Literature 1: WO 96/30346

Non Patent Literature

Non Patent Literature 1: Invest New Drugs 26 (5): 445-54, 2008.
Non Patent Literature 2: Lancet Oncol. 13 (10): 993-1001, 2012.
Non Patent Literature 3: Oncologist. 6(1): 66-80, 2001.
Non Patent Literature 4: Eur J Cancer. 43(1): 175-83, 2007.

SUMMARY OF INVENTION

Technical Problem

The object of the present invention is to provide a novel combination therapy for solid cancers using an FTD/TPI combination drug which exhibits remarkable antitumor effects, and few side effects.

Solution to Problem

In view of this situation, when a combination therapy comprising repeating a 28-day cycle consisting of two times of 5-days' administration at a dose of 70 mg/m$^2$/day with 2-days' rest of an FTD/TPI combination drug, followed by rest of the drug administration for 2 weeks, and an administration of CPT-11 at a dose of 150 mg/m$^2$/day once in 2 weeks was performed in a colorectal cancer patient on the basis of the dose at which effects of each drug have previously been reported as in Reference Example described later, only about 30% of the predetermined amount of CPT-11 could be administered because side effects such as neutropenia, diarrhea, and body weight loss appeared strongly. As a result of repeated studies on administration schedule which can suppress the occurrence of side effects and in which a predetermined amount can be administered, the present inventors have found that a combination therapy comprising administering an FTD/TPI combination drug at a dose in the range of 35 to 70 mg/m$^2$/day as a reduced amount of FTD, and CPT-11 at a dose in the range of 45 to 144 mg/m$^2$/day to a solid cancer patient suppresses the occurrence of side effects and exerts a superior antitumor effects.

That is, the present invention provides the following inventions [1] to [32].

[1] An antitumor agent for solid cancers, wherein a combination drug containing trifluridine and tipiracil hydrochloride in a molar ratio of 1:0.5 is administered, using a reduced amount of trifluridine, at a dose in the range of 35 to 70 mg/m$^2$/day, and irinotecan hydrochloride hydrate is administered at a dose in the range of 45 to 144 mg/m$^2$/day.

[2] The antitumor agent according to [1], wherein the combination drug containing trifluridine and tipiracil hydrochloride in a molar ratio of 1:0.5 is administered at a dose of 70 mg/m$^2$/day using a reduced amount of trifluridine.

[3] The antitumor agent according to [1] or [2], wherein irinotecan hydrochloride hydrate is administered at a dose in the range of 75 to 120 mg/m$^2$/day.

[4] The antitumor agent according to any one of [1] to [3], wherein the solid cancer is colorectal cancer, lung cancer, breast cancer, pancreatic cancer, or gastric cancer.

[5] The antitumor agent according to any one of [1] to [4], wherein one cycle of an administration schedule, in which, in a period of 28 days, a combination drug containing trifluridine and tipiracil hydrochloride in a molar ratio of 1:0.5 is administered on Days 1 to 5 and on Days 8 to 12, and CPT-11 is administered on Day 1 and on Day 15, is repeated once or twice or more times.

[6] An agent for potentiating antitumor effect comprising a combination drug containing trifluridine and tipiracil hydrochloride in a molar ratio of 1:0.5 for enhancing the antitumor effect of irinotecan hydrochloride hydrate in a solid cancer patient, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[7] An antitumor agent comprising a combination drug containing trifluridine and tipiracil hydrochloride in a molar ratio of 1:0.5 for treating a solid cancer patient who has received irinotecan hydrochloride hydrate, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[8] A kit preparation comprising an antitumor agent containing a combination drug of trifluridine and tipiracil hydrochloride in a molar ratio of 1:0.5 and an instruction for use, wherein the instruction for use describes that the combination drug of trifluridine and tipiracil hydrochloride in a molar ratio of 1:0.5 is to be administered to a solid cancer patient, using a reduced amount of trifluridine, at a dose in the range of 35 to 70 mg/m²/day, and irinotecan hydrochloride hydrate is to be administered at a dose in the range of 45 to 144 mg/m²/day.

[9] A combination drug containing trifluridine and tipiracil hydrochloride in a molar ratio of 1:0.5 for treating a solid cancer, wherein the combination drug containing trifluridine and tipiracil hydrochloride in a molar ratio of 1:0.5 is administered, using a reduced amount of trifluridine at a dose in the range of 35 to 70 mg/m²/day, and irinotecan hydrochloride hydrate is administered at a dose in the range of 45 to 144 mg/m²/day.

[10] The combination drug according to [9], wherein the combination drug containing trifluridine and tipiracil hydrochloride in a molar ratio of 1:0.5 is administered, using a reduced amount of trifluridine, at a dose of 70 mg/m²/day.

[11] The combination drug according to [9] or [10], wherein irinotecan hydrochloride hydrate is administered at a dose in the range of 75 to 120 mg/m²/day.

[12] The combination drug according to any one of [9] to [11], wherein the solid cancer is colorectal cancer, lung cancer, breast cancer, pancreatic cancer, or gastric cancer.

[13] The combination drug according to any one of [9] to [12], wherein one cycle of an administration schedule, in which, in a period of 28 days, the combination drug containing trifluridine and tipiracil hydrochloride in a molar ratio of 1:0.5 is administered on Days 1 to 5 and on Days 8 to 12, and CPT-11 is administered on Days 1 and 15, is repeated once or twice or more times.

[14] A combination drug containing trifluridine and tipiracil hydrochloride in a molar ratio of 1:0.5 for enhancing the antitumor effect of irinotecan hydrochloride hydrate in a solid cancer patient, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[15] A combination drug containing trifluridine and tipiracil hydrochloride in a molar ratio of 1:0.5 for treating a solid cancer patient who has received irinotecan hydrochloride hydrate, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[16] Use of a combination drug containing trifluridine and tipiracil hydrochloride in a molar ratio of 1:0.5 for manufacturing an antitumor agent against solid cancers, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[17] The use according to claim 16, wherein the combination drug containing trifluridine and tipiracil hydrochloride in a molar ratio of 1:0.5 is administered, using a reduced amount of trifluridine, at a dose of 70 mg/m²/day.

[18] The use according to [16] or [17], wherein irinotecan hydrochloride hydrate is administered at a dose in the range of 75 to 120 mg/m²/day.

[19] The use according to anyone of [16] to [18], wherein the solid cancer is colorectal cancer, lung cancer, breast cancer, pancreatic cancer, or gastric cancer.

[20] The use according to anyone of [16] to [19], wherein one cycle of an administration schedule, in which, in a period of 28 days, the combination drug containing trifluridine and tipiracil hydrochloride in a molar ratio of 1:0.5 is administered on Days 1 to 5 and on Days 8 to 12, and CPT-11 is administered on Days 1 and 15, is repeated once or twice or more times.

[21] Use for manufacturing an agent for potentiating antitumor effect comprising a combination drug containing trifluridine and tipiracil hydrochloride in a molar ratio of 1:0.5 to potentiate the antitumor effect of irinotecan hydrochloride hydrate in a solid cancer patient, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[22] Use for manufacturing an antitumor agent comprising a combination drug containing trifluridine and tipiracil hydrochloride in a molar ratio of 1:0.5 to treat a solid cancer patient who has received irinotecan hydrochloride hydrate, wherein the combination drug containing trifluridine and tipiracil hydrochloride in a molar ratio of 1:0.5 is administered, using a reduced amount of trifluridine, at a dose in the range of 35 to 70 mg/m²/day, and irinotecan hydrochloride hydrate is administered at a dose in the range of 45 to 144 mg/m²/day.

[23] A method for treating a solid cancer, wherein a combination drug containing trifluridine and tipiracil hydrochloride in a molar ratio of 1:0.5 is administered, using a reduced amount of trifluridine, to a solid cancer patient at a dose in the range of 35 to 70 mg/m²/day, and irinotecan hydrochloride hydrate is administered at a dose in the range of 45 to 144 mg/m²/day.

[24] The method according to [23], wherein the combination drug containing trifluridine and tipiracil hydrochloride in a molar ratio of 1:0.5 is administered at a dose of 70 mg/m²/day, using a reduced amount of trifluridine.

[25] The method according to [23] or [24], wherein irinotecan hydrochloride hydrate is administered at a dose in the range of 75 to 120 mg/m²/day.

[26] The method according to any one of [23] to [25], wherein the solid cancer is colorectal cancer, lung cancer, breast cancer, pancreatic cancer, or gastric cancer.

[27] The method according to any one of [23] to [26], wherein one cycle of an administration schedule, in which, in a period of 28 days, the combination drug containing trifluridine and tipiracil hydrochloride in a molar ratio of 1:0.5 is administered on Days 1 to 5 and on Days 8 to 12 and CPT-11 is administered on Days 1 and 15, is repeated once or twice or more times.

[28] A method for enhancing the antitumor effect of irinotecan hydrochloride hydrate against solid cancer patients, wherein a combination drug containing trifluridine and tipiracil hydrochloride in a molar ratio of 1:0.5 is administered, using a reduced amount of trifluridine, to a solid cancer patient at a dose in the range of 35 to 70 mg/m$^2$/day, and irinotecan hydrochloride hydrate is administered at a dose in the range of 45 to 144 mg/m$^2$/day.

[29] A method for treating a solid cancer patient who has received irinotecan hydrochloride hydrate, wherein a combination drug containing trifluridine and tipiracil hydrochloride in a molar ratio of 1:0.5 is administered, using a reduced amount of trifluridine, at a dose in the range of 35 to 70 mg/m$^2$/day to a solid cancer patient, and irinotecan hydrochloride hydrate is administered at a dose in the range of 45 to 144 mg/m$^2$/day.

[30] An antitumor agent for solid cancers, wherein a combination drug containing trifluridine and tipiracil hydrochloride in a molar ratio of 1:0.5 is administered in combination with irinotecan hydrochloride hydrate, wherein the dose of the combination drug containing trifluridine and tipiracil hydrochloride in a molar ratio of 1:0.5 is 50% to 100% of the recommended dose in the monotherapy, and the dose of irinotecan hydrochloride hydrate is 25% to 80% of the recommended dose in the monotherapy.

[31] The antitumor agent according to [30], wherein the dose of the combination drug containing trifluridine and tipiracil hydrochloride in a molar ratio of 1:0.5 is 100% of the recommended dose in the monotherapy.

[32] The antitumor agent according to [30] or [31], wherein the dose of irinotecan hydrochloride hydrate is 50% to 70% of the recommended dose in the monotherapy.

Advantageous Effects of Invention

According to the antitumor agent of the present invention, it is possible to perform cancer treatment exhibiting a high antitumor effect while suppressing the onset of side effects, thereby achieving long-term survival in patients.

DESCRIPTION OF EMBODIMENTS

Figure 1:
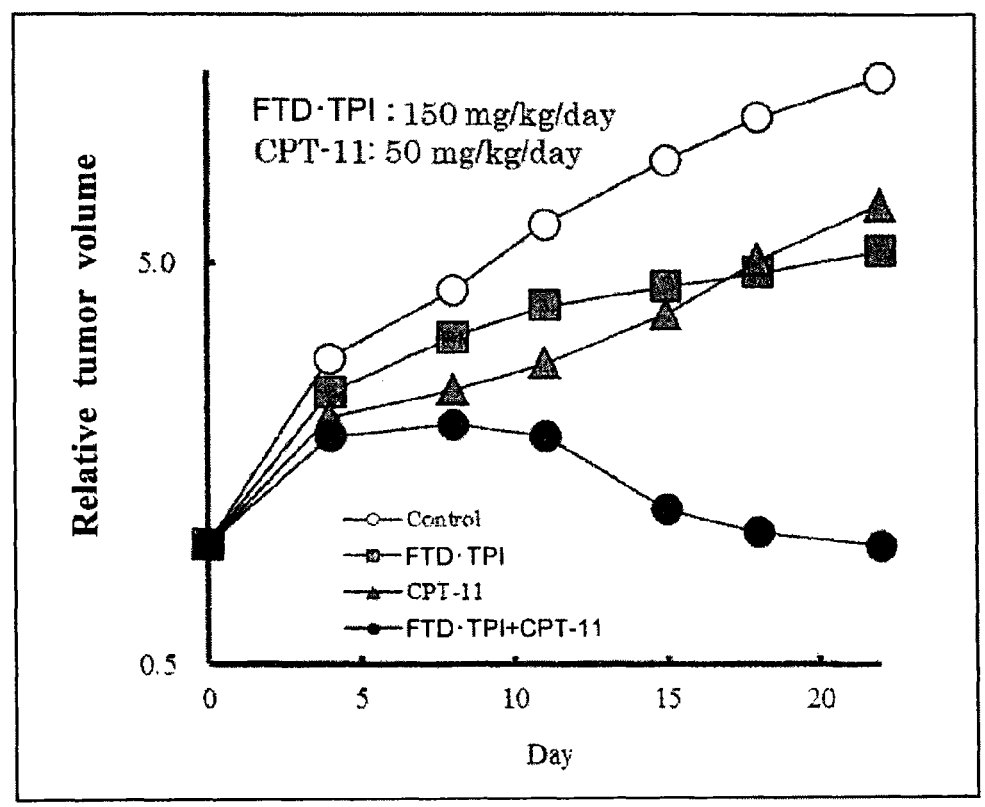
FIG. 1 is a graph showing an antitumor effect by combination use of an FTD/TPI combination drug at a dose of 150 mg/kg/day and CPT-11 at a dose of 50 mg/kg/day.
Figure 2:
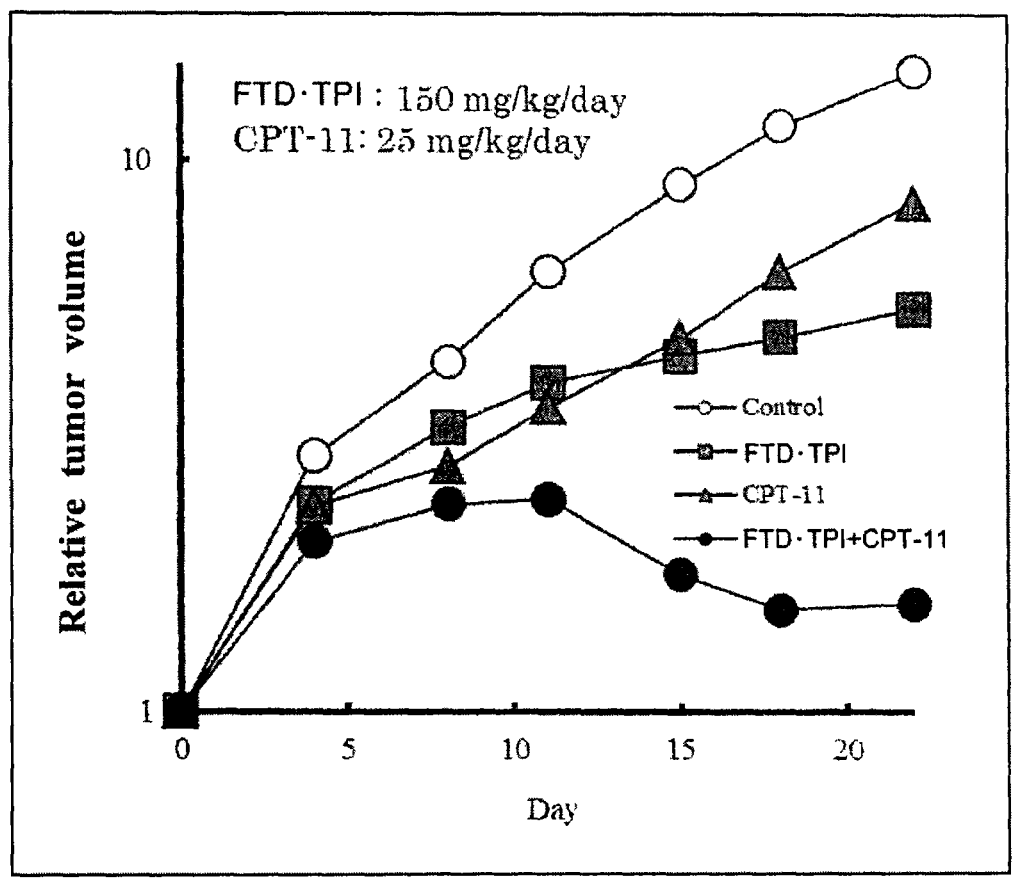
FIG. 2 is a graph showing an antitumor effect by combination use of an FTD/TPI combination drug at a dose of 150 mg/kg/day and CPT-11 at a dose of 25 mg/kg/day.
Figure 3:
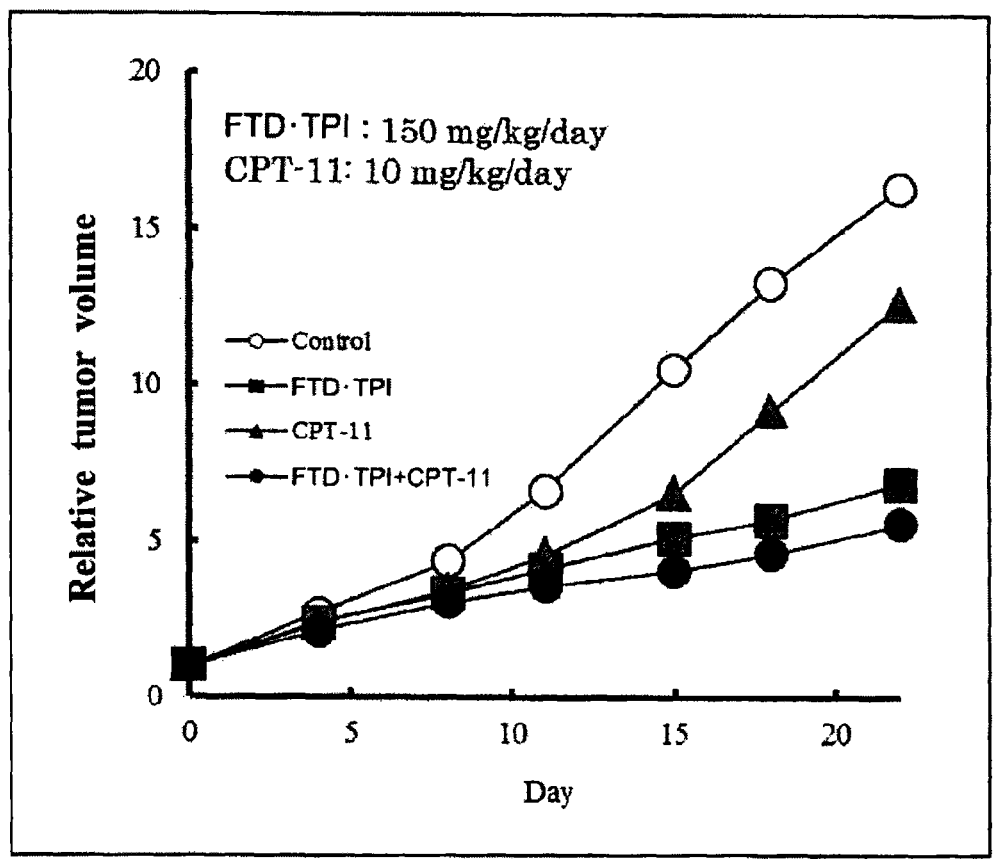
FIG. 3 is a graph showing an antitumor effect by combination use of an FTD/TPI combination drug at a dose of 150 mg/kg/day and CPT-11 at a dose of 10 mg/kg/day.
Figure 4:
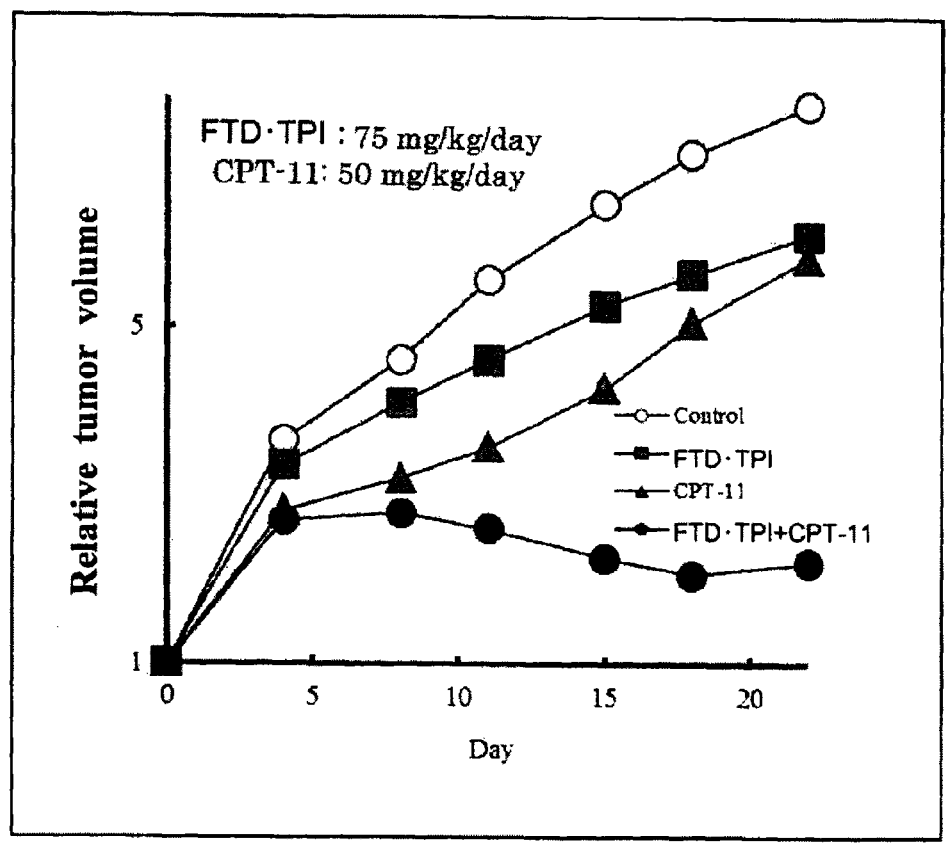
FIG. 4 is a graph showing an antitumor effect by combination use of an FTD/TPI combination drug at a dose of 75 mg/kg/day and CPT-11 at a dose of 50 mg/kg/day.
Figure 5:
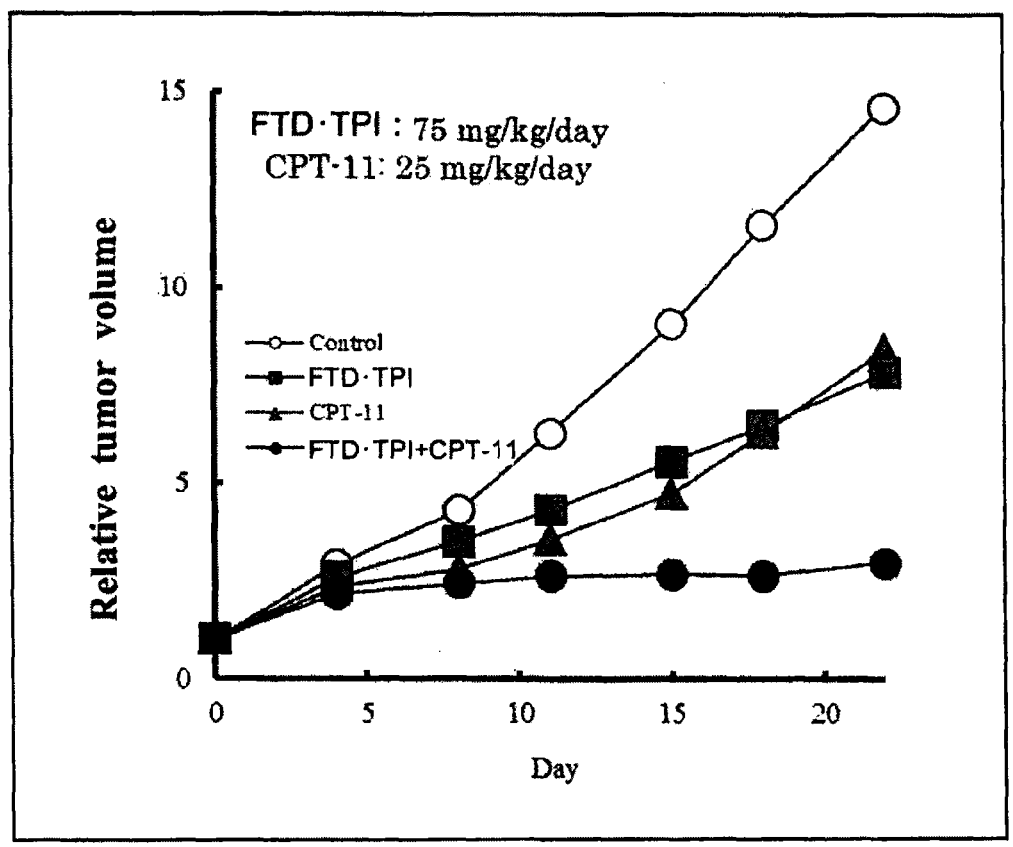
FIG. 5 is a graph showing an antitumor effect by combination use of an FTD/TPI combination drug at a dose of 75 mg/kg/day and CPT-11 at a dose of 25 mg/kg/day.
Figure 6:
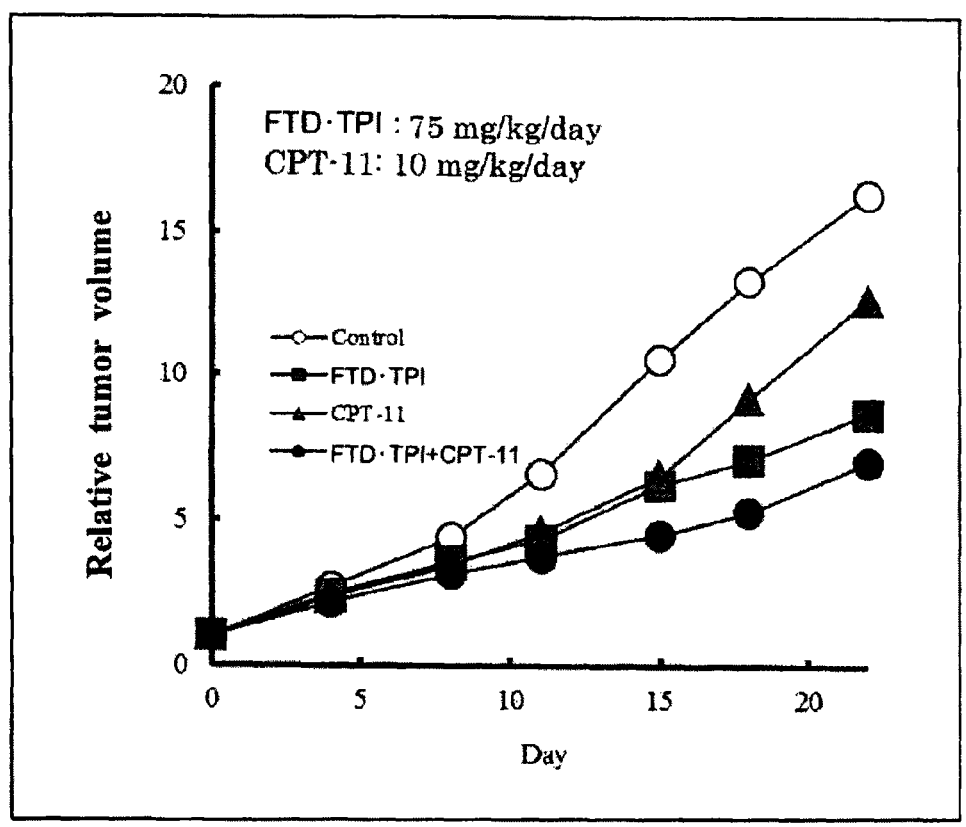
FIG. 6 is a graph showing an antitumor effect by combination use of an FTD/TPI combination drug at a dose of 75 mg/kg/day and CPT-11 at a dose of 10 mg/kg/day.

FTD and TPI of the present invention are both known compounds and can be synthesized, for example, according to the method described in WO 96/30346. A combination drug of FTD and TPI in a molar ratio of 1:0.5 is also known (Non Patent Literatures 1 and 2).

CPT-11 of the present invention is a known compound and can be synthesized according to the method described in Japanese Patent No. 3,004,077. Also, the commercially available product, for example, CAMPTO (registered trademark, Yakult Honsha Co., Ltd.), may be used.

The administration schedule of the antitumor agent of the present invention is not particularly limited as long as the effects of the present invention are achieved, and one cycle in which, in a period of 28 days, a combination drug containing FTD and TPI in a molar ratio of 1:0.5 is administered on Days 1 to 5 and on Days 8 to 12, and CPT-11 is administered on Days 1 and 15, is preferably repeated once or twice or more times.

As shown in Reference Example and Examples described later, when 50% to 100% of the recommended dose of FTD/TPI combination drug in the monotherapy in mice was administered to mice in combination with 25% to 80% of the recommended dose of CPT-11 in the monotherapy in mice, superior antitumor effects and suppression of side effects could be achieved. Thus, the dose of FTD/TPI combination drug is 50% to 100%, especially preferably 100%, of the recommended dose in the monotherapy in humans from the viewpoint of a balance between antitumor effects and side effects. The dose of CPT-11 is 25% to 80%, preferably 40% to 80%, more preferably 50% to 80%, especially preferably 50% to 70%, of the recommended dose in the monotherapy in humans from the viewpoint of a balance between antitumor effects and side effects.

In other words, since the recommended dose of FTD/TPI combination drug in the monotherapy in humans is 70 mg/m$^2$/day, the dose of FTD is 35 to 70 mg/m$^2$/day, and from the viewpoint of a balance between antitumor effects and side effects, the dose of FTD is especially preferably 70 mg/m$^2$/day.

The recommended dose of CPT-11 in the monotherapy in humans may vary depending on the administration schedules, for example, for administration every two weeks, the dose of CPT-11 is 150 to 180 mg/m$^2$/day. Thus, when the recommended dose of CPT-11 is 180 mg/m$^2$/day (for example, for gastrointestinal cancer, lung cancer, breast cancer, cervical cancer, or ovarian cancer, preferably for colorectal cancer and pancreatic cancer), the dose of CPT-11 according to the present invention is in the range of 45 to 144 mg/m$^2$/day, and from the viewpoint of a balance between antitumor effects and side effects, the dose of CPT-11 is preferably in the range of 72 to 144 mg/m$^2$/day, more preferably in the range of 90 to 144 mg/m$^2$/day, and especially preferably in the range of 90 to 126 mg/m$^2$/day. Also, when the recommended dose is 150 mg/m$^2$/day (for example, for gastrointestinal cancer, lung cancer, breast cancer, cervical cancer, or ovarian cancer, preferably for cervical cancer, ovarian cancer, gastric cancer, and colorectal cancer), the dose of CPT-11 according to the present invention is in the range of 37.5 to 120 mg/m$^2$/day and from the viewpoint of a balance between antitumor effects and side effects, the dose of CPT-11 is preferably in the range of 60 to 120 mg/m$^2$/day, more preferably in the range of 75 to 120 mg/m$^2$/day, and especially preferably in the range of 75 to 105 mg/m$^2$/day.

Further, in the case of administration every week, the recommended dose of CPT-11 in the monotherapy in humans is 100 to 125 mg/m$^2$/day. While the recommended dose is 100 mg/m$^2$/day (for example, for gastrointestinal cancer, lung cancer, breast cancer, cervical cancer, or ovarian cancer, preferably for small cell lung cancer, non-small cell lung cancer, breast cancer, cervical cancer, ovarian cancer, gastric cancer, and colorectal cancer), the dose of CPT-11 according to the present invention is in the range of 25 to 80 mg/m$^2$/day and from the viewpoint of a balance between antitumor effects and side effects, the dose of CPT-11 is preferably 40 to 80 mg/m$^2$/day, more preferably 50 to 80 mg/m$^2$/day, and especially preferably 50 to 70 mg/m$^2$/day. In addition, when the recommended dose is 125 mg/m$^2$/day (for example, for gastrointestinal cancer, lung cancer, breast cancer, cervical cancer or ovarian cancer, and preferably for colorectal cancer), the dose of CPT-11 according to the present invention is in the range of 31.25 to 100 mg/m$^2$/day and from the viewpoint of a balance between antitumor effects and side effects, the dose of CPT-11 is preferably in the range of 50 to 100 mg/m$^2$/day, more preferably in the range of 62.5 to 100 mg/m$^2$/day, and especially preferably in the range of 62.5 to 87.5 mg/m$^2$/day.

In addition, in the case of administration every three weeks, the recommended dose of CPT-11 in the monotherapy in humans is 350 mg/m$^2$/day (for example, for gastrointestinal cancer, lung cancer, breast cancer, cervical cancer, or ovarian cancer, and preferably for colorectal cancer). Whereas, the dose of CPT-11 according to the present invention is in the range of 87.5 to 280 mg/m$^2$/day and from the viewpoint of a balance between antitumor effects and side effects, the dose of CPT-11 is preferably in the range of 140 to 280 mg/m$^2$/day, more preferably in the range of 175 to 280 mg/m$^2$/day, and especially preferably in the range of 175 to 245 mg/m$^2$/day.

The target of the antitumor agent of the present invention is a solid cancer including specifically head and neck cancer, gastrointestinal cancer (esophageal cancer, gastric cancer, duodenal cancer, liver cancer, biliary tract cancer (gallbladder cancer/bile duct cancer), pancreatic cancer, small intestinal cancer, large intestinal cancer (colorectal cancer, colon cancer, rectal cancer), etc.), lung cancer, breast cancer, ovarian cancer, uterine cancer (cervical cancer, uterine cancer), renal cancer, bladder cancer, prostate cancer, etc. Of these, from the viewpoint of antitumor effects and side effects, the target is preferably gastrointestinal cancer, lung cancer, breast cancer, cervical cancer, or ovarian cancer; more preferably colorectal cancer, lung cancer, breast cancer, pancreatic cancer, or gastric cancer; more preferably colorectal cancer and gastric cancer; and particularly preferably colorectal cancer. Here, the solid cancer includes not only primary tumor but also tumor derived from solid cancer that has metastasized to other organs (such as liver). Also, the antitumor agent of the present invention may be one used for postoperative adjuvant chemotherapy that is performed for preventing the recurrence after having surgically removed the tumor.

Since the administration means and the administration schedule are different in each active ingredient, all the active ingredients cannot be formulated in one dosage form. Thus, the antitumor agent of the present invention is formulated separately for each active ingredient into a plurality of dosage forms. It is preferred that FTD and TPI are formulated as a combination drug and CPT-11 is formulated as a single agent.

Further, as long as each active ingredient is administered according to the dose of the present invention, each preparation may be manufactured and sold together in a single package suitable for combined administration, or each preparation may be manufactured and sold after being divided into a separate package.

There is no particular limitation to the dosage form of the antitumor agent of the present invention, and it can be appropriately selected depending on the therapeutic purposes and includes specifically oral preparations (tablets, coated tablets, powders, granules, capsules, solutions, etc.), injections, suppositories, patches, ointments, etc. An oral preparation is preferable for the combination drug of FTD and TPI, and an injectable preparation is preferable for CPT-11.

Depending on the dosage form, the antitumor agent of the present invention can be usually prepared by the known method using a pharmaceutically acceptable carrier. Such a carrier includes various ones which are commonly used in conventional drugs, such as excipients, binders, disintegrators, lubricants, diluents, solubilizers, suspending agents, isotonic agents, pH adjusting agents, buffering agents, stabilizers, coloring agents, flavoring agents, and flavors.

The present invention also relates to an agent for potentiating antitumor effect comprising an FTD/TPI combination drug for enhancing the antitumor effect of CPT-11 in a solid cancer patient (especially colorectal cancer patient), wherein the FTD/TPI combination drug and CPT-11 are administered on the basis of the dose mentioned above. The agent for potentiating antitumor effect has the dosage form of the above antitumor agent.

The present invention further relates to an antitumor agent comprising an FTD/TPI combination drug for treating a solid cancer patient (especially colorectal cancer patient) who has received CPT-11, wherein the FTD/TPI combination drug and CPT-11 are administered based on the dose mentioned above. The antitumor agent has the above dosage form.

The present invention furthermore relates to a kit preparation comprising an FTD/TPI combination drug and an instruction for use teaching that the FTD/TPI combination drug and CPT-11 are to be administered to a solid cancer patient (especially colorectal cancer patient) based on the dose mentioned above. Here, the term "instruction for use" may be anyone as long as it describes the dose; however, an instruction for use, in which the above dose is recommended though legal binding force does not matter, is preferable. The instruction for use includes specifically a package insert, a pamphlet, etc. Also, a kit preparation comprising an instruction for use may be one in which the instruction for use is printed on or attached to the package of the kit preparation, or a kit preparation may be one in which an antitumor agent together with the instruction for use is enclosed in a package of the kit preparation.

EXAMPLES

Then, the present invention is explained in more detail by way of Examples.

Reference Example

Cultured cells (1×10$^7$ cells/mouse) of human colon cancer cell line (KM20C) were intraperitoneally transplanted into 5-6 weeks old BALB/cA Jcl-nu mice after birth, and the mice were assigned to each group so that the mean body weight of each group became equal. The date on which such grouping (n=10) was performed was taken as Day 0.

An FTD/TPI combination drug (a mixture of FTD and TPI in a molar ratio of 1:0.5) was prepared so as to be 75, 100, 150, 300, and 450 mg/kg/day as FTD. Since a death case of irinotecan hydrochloride hydrate (CPT-11: CAMPTO (registered trademark) infusion, Yakult Honsha Co., Ltd.) at a dose of 111 mg/kg/day was reported (Kiso to Rinsho, (1990), Vol. 24, No. 14, 7-17), irinotecan hydrochloride hydrate was prepared so as to be 80 and 100 mg/kg/day. Starting the dug administration from Day 3, a 5-days' daily oral administration of the FTD/TPI combination drug with 2-days' rest was performed for 6 weeks, and CPT-11 was administered once in a week from the tail vein for 6 weeks.

As an index of the antitumor effect, the number of survivors of each group of mice and the survival time of each group was compared. The results are shown in Table 1.

TABLE 1

| Drug | Dose (mg/kg/day) | Treatmet[a] | No. of animals | Survival time (day) Mean ± SD | ILS[b] (%) |
|---|---|---|---|---|---|
| Control | — | — | 10 | 40.0 ± 4.3 | — |
| FTD•TPI | 75 | 5-days' oral administration with 2-days' rest (b.i.d) | 10 | 50.0 ± 9.1 | 25.0 |
| FTD•TP1 | 100 | 5-days' oral administration with 2-days' rest (b.i.d) | 10 | 75.8 ± 42.6 | 89.5 |
| FTD•TPI | 150 | 5-days' oral administration with 2-days' rest (b.i.d) | 10 | 125.7 ± 64.8 | 214.3 |
| FTD•TP1 | 300 | 5-days' oral administration with 2-days' rest (b.i.d) | 10 | 75.6 ± 17.5 | 89.0 |
| FTD•TPI | 450 | 5-days' oral administration with 2-days' rest (b.i.d) | 10 | 54.1 ± 18.3 | 35.3 |
| CTP-11 | 80 | i.v., weekly | 10 | 61.6 ± 12.6 | 54.0 |
| CTP-11 | 100 | i.v., weekly | 10 | 72.5 ± 12.3 | 81.3 |

[a]Drugs were given for 6 weeks from Day 3.
[b]ILS means increase in life span.
ILS (%) = [(mean survival time of treatment group)/(mean survival time of control group) − 1] × 100

As described in Table 1, since the life span of a 100 mg/kg/day administration group of CPT-11 in mice was long, the recommended dose (RD) of CPT-11 in mice is 100 mg/kg/day as irinotecan hydrochloride hydrate. Thus, the dose of 100 mg/kg/day in mice is equivalent to RD of 150 to 180 mg/m$^2$/day in humans.

Since the life span was long in the 150 mg/kg/day (as a reduced amount of FTD) administration group of FTD/TPI combination drug, RD of the FTD/TPI combination drug in mice is 150 mg/kg/day using a reduced amount of FTD. Thus, 150 mg/kg/day (as a reduced amount of FTD) in mice is equivalent to RD of 70 mg/m$^2$/day (as a reduced amount of FTD) in humans.

Example 1

Human colon cancer cell lines (KM20C) were transplanted into the right chest of 5-6 weeks old BALB/cA Jcl-nu mice after birth. After tumor transplant, the major axis (mm) and minor axis (mm) of tumor were measured, and the tumor volume (TV) was calculated. Then, the animals were assigned to each group so that the mean TV of each group becomes equal and the day when grouping (n=6) was performed was taken as Day 0.

The FTD/TPI combination drug (a mixture of FTD and TPI in a molar ratio of 1:0.5) was prepared so as to be 75 and 150 mg/kg/day as FTD. CPT-11 (CAMPTO (registered trademark, Yakult Honsha Co., Ltd.) infusion) was prepared so as to be 10, 25, and 50 mg/kg/day as irinotecan hydrochloride hydrate. The FTD/TPI combination drug was daily and orally administered on Days 1 to 14, and CPT-11 was administered via the tail vein on Days 1 and 8. The FTD/TPI combination drug and CPT-11 were administered to the combined administration group at the same dose according to the administration schedule as in the monotherapy group. A list of each drug administration group is shown in Table 2.

As an indicator of the antitumor effect, TV on Days 4, 8, 11, 15, 18, and 22 in each group was calculated, and the relative tumor volume (RTV) on Day 0 was determined by the following equation, and then plotted. The daily changes of the RTV of the untreated group (control), the FTD/TPI combination drug administration group, the CPT-11 administration group, and the combined administration group of FTD/TPI combination drug and CPT-11 were compared.

$$TV\ (mm^3) = (long\ axis \times (short\ axis)^2)/2$$

$$RTV = (TV\ on\ Day\ 28)/(TV\ on\ Day\ 0)$$

TABLE 2

| Drug | Dose (mg/kg/day) | Treatment |
|---|---|---|
| FTD•TPI | 75 | Day 1-14, p.o. |
|  | 150 |  |
| CPT-11 | 10 | Day 1 and 8, i.v. |
|  | 25 |  |
|  | 50 |  |
| FTD•TPI + CPT-11 | 75 + 10 | Day 1-14, p.o. |
|  | 75 + 25 | (FTD•TPI) |
|  | 75 + 50 | Day 1 and 8, i.v. |
|  | 150 + 10 | (CPT-11) |
|  | 150 + 25 |  |
|  | 150 + 50 |  |

As shown in FIGS. 1 to 6, when the dose of FTD/TPI combination drug was in the range of 75 to 150 mg/kg/day and the dose of CPT-11 was in the range of 25 to 50 mg/kg/day, a synergistic antitumor effect was obtained.

Example 2

Cultured cells (1×10$^7$ cells/mouse) of a human colon cancer cell line (KM20C) were intraperitoneally transplanted into 5-6 weeks old mice after birth, BALE/cA Jcl-nu mice. The mice were assigned to each group (n=10) so that the mean body weight of each group became equal, and the day when such grouping (n=6) was performed was taken as Day 0.

A FTD/TPI combination drug (mixture of FTD and TPI in a molar ratio of 1:0.5) was prepared so as to be 150 mg/kg/day (recommended dose) as FTD. CPT-11 (CAMPTO (registered trademark) infusion, Yakult Honsha Co., Ltd.) was prepared so as to be 50, 70, and 100 mg/kg/day as irinotecan hydrochloride hydrate. In each combined administration group, the combined administration was started on Day 3 and the FTD/TPI combination drug was subjected to a 5-days' daily oral administration with 2-days' rest for 6 weeks, and the CPT-11 was administered once a week via the tail vein for 6 weeks.

As an indicator of the antitumor effect, the number of survivors in each group of mice on Day 70 was confirmed and the survival rate of each group was compared. The survival rate of each group on Day 70 is shown in FIG. 7.

Figure 7:
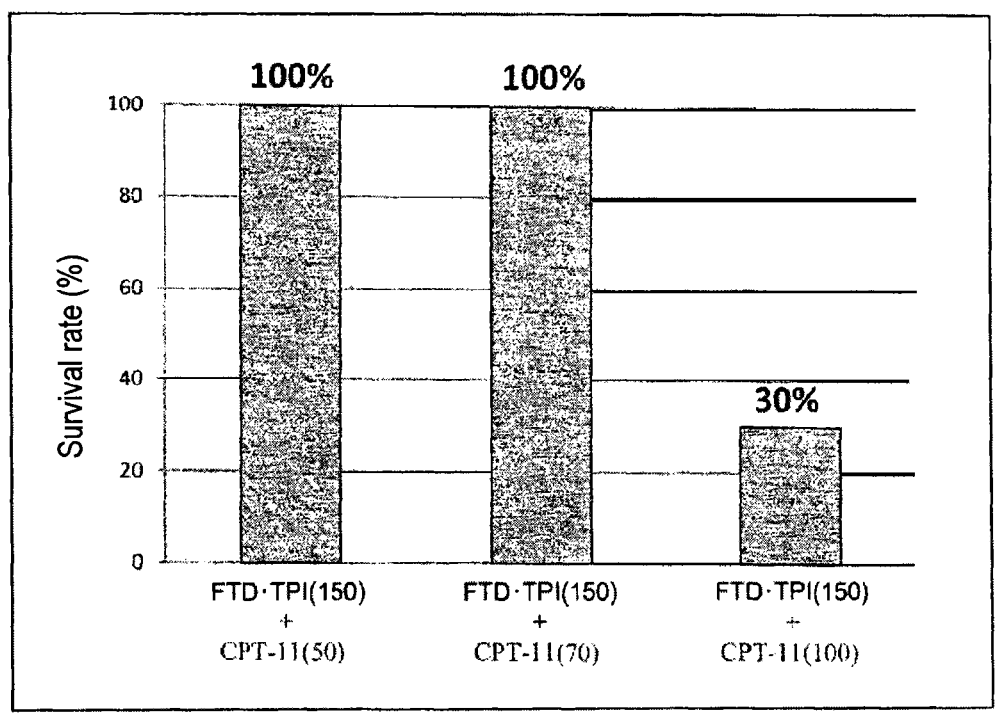
FIG. 7 is a graph showing survival rate at Day 70 in each combined administration group of an FTD/TPI combination drug at a dose of 150 mg/kg/day and CPT-11 at a dose of 50, 70, or 100 mg/kg/day.

As shown in FIG. 7, in the administration group of 150 mg/kg/day of FTD/TPI combination drug and 50 or 70 mg/kg/day of CPT-11, the survival rate on Day 70 was 100%, while in the administration group of 150 mg/kg/day of FTD/TPI combination drug and 100 mg/kg/day of CPT-11, side effects appeared strongly and the survival rate on Day 70 was extremely lowered up to 30%.

Example 3

A combined administration test of an FTD/TPI combination drug and CPT-11 was performed in the same manner as in Example 1, except that the cell line was changed to human gastric cancer cell line (SC-2). The FTD/TPI combination drug (a mixture of FTD and TPI in a molar ratio of 1:0.5) was prepared so as to be 75 and 150 mg/kg/day (recommended dose) as FTD, and CPT-11 was prepared so as to be 40 and 80 mg/kg/day as irinotecan hydrochloride hydrate. The results are shown in Table 3.

TABLE 3

| Drug | Dose (mg/kg/day) | Treatment | RTV [a] (mean ± SD) | TGI [b] (%) |
|---|---|---|---|---|
| Control | — | — | 12.59 ± 0.87 | — |
| FTD•TPI | 75 | Day 1~14, | 6.99 ± 0.45 ** | 44.5 |
| FTD•TPI | 150 | p.o., b.i.d. | 4.91 ± 0.28 ** | 61.0 |
| CPT-11 | 40 | Day 1, 8, i.v., | 4.46 ± 0.47 ** | 64.6 |
| CPT-11 | 80 | q.d. | 2.59 ± 0.21 ** | 79.4 |
| FTD•TPI + CPT-11 | 75 + 40 | Day 1~14, p.o., b.i.d. (FTD•TPI) | 2.39 ± 0.35 **## | 81.0 |
| FTD•TPI + CPT-11 | 75 + 80 | Day 1, 8, i.v., q.d.(CPT-11) | 1.24 ± 0.19 **## | 90.2 |
| FTD•TPI + CPT-11 | 150 + 40 | Day 1~14, p.o., b.i.d. (FTD•TPI) | 1.52 ± 0.15 **## | 87.9 |
| FTD•TPI + CPT-11 | 150 + 80 | Day 1, 8, i.v., q.d.(CPT-11) | 0.95 ± 0.10 **## | 92.5 |

** p < 0.01 with Aspin-Welch's t-test as compared with the control group.
overall maximal p < 0.01 by closed testing procedure (Intersection-Union Test).
[a] Relative tumor volume (RTV) on Day 15 was calculated as the ratio of TV an Day 15 to that on Day 0 according to th RTV = (TV on Day 15)/(TV on Day 0)
[b] Tumor growth inhibition rate (TGI) on Day 15 on the basis of RTV was calculated according to the following formula TGI (%) = [1 − (mean RTV of the treated group)/(mean RTV of the control group)] × 100

As shown in Table 3, when 50 to 100% of the recommended dose of FTD/TPI combination drug in the monotherapy was used in combination with 40 to 80% of the recommended dose of CPT-11 in the monotherapy for gastric cancer, a remarkable enhancement of the antitumor effect was confirmed. Also, the body weight loss was within an acceptable range.

From the above, when 50 to 100% of the recommended dose of FTD/TPI combination drug in the monotherapy and 25 to 80% of the recommended dose of CPT-11 in the monotherapy were used in combination, it was revealed that an excellent antitumor effect was exhibited while suppressing the onset of side effects.

The invention claimed is:

1. A method for treating a solid cancer, comprising: administering to a subject a combination drug comprising trifluridine and tipiracil hydrochloride in a molar ratio of 1:0.5 at a dose of 35 to 70 mg/m$^2$/day of trifluridine, and 45 to 144 mg/m$^2$/day of irinotecan hydrochloride hydrate.

2. The method according to claim 1, wherein the combination drug is administered at a dose of 70 mg/m$^2$/day of trifluridine.

3. The method according to claim 1, wherein 75 to 120 mg/m$^2$/day of irinotecan hydrochloride hydrate is administered.

4. The method according to claim 1, wherein the solid cancer is colorectal cancer, lung cancer, breast cancer, pancreatic cancer, or gastric cancer.

5. The method according to claim 1, wherein, in a period of 28 days, the combination drug is administered on Days 1 to 5 and Days 8 to 12, and irinotecan hydrochloride hydrate is administered on Days 1 and 15.

6. A method for enhancing an antitumor effect of irinotecan hydrochloride hydrate against a solid cancer, comprising:
administering to a subject a combination drug comprising trifluridine and tipiracil hydrochloride in a molar ratio of 1:0.5 at a dose of 35 to 70 mg/m$^2$/day of trifluridine, and 45 to 144 mg/m$^2$/day of irinotecan hydrochloride hydrate.

7. A method for treating a patient having a solid cancer who has received irinotecan hydrochloride hydrate, comprising:
administering to the patient a combination drug comprising trifluridine and tipiracil hydrochloride in a molar ratio of 1:0.5 at a dose of 35 to 70 mg/m$^2$/day of trifluridine, and 45 to 144 mg/m$^2$/day of irinotecan hydrochloride hydrate.

8. The method according to claim 1, wherein the dose of the combination drug is 100% of a recommended dose in monotherapy.

9. The method according to claim 1, wherein the dose of irinotecan hydrochloride hydrate is 50% to 70% of a recommended dose in monotherapy.

10. The method according to claim 5, wherein the period of 28 days is repeated a plurality of times.

11. The method according to claim 6, wherein the combination drug is administered at a dose of 70 mg/m$^2$/day of trifluridine.

12. The method according to claim 7, wherein the combination drug is administered at a dose of 70 mg/m$^2$/day of trifluridine.

13. The method according to claim 6, wherein, in a period of 28 days, the combination drug is administered on Days 1 to 5 and Days 8 to 12, and irinotecan hydrochloride hydrate is administered on Days 1 and 15.

14. The method according to claim 13, wherein the period of 28 days is repeated a plurality of times.

15. The method according to claim 7, wherein, in a period of 28 days, the combination drug is administered on Days 1 to 5 and Days 8 to 12, and irinotecan hydrochloride hydrate is administered on Days 1 and 15.

16. The method according to claim 15, wherein the period of 28 days is repeated a plurality of times.

17. The method according to claim 6, wherein the solid cancer is colorectal cancer, lung cancer, breast cancer, pancreatic cancer, or gastric cancer.

18. The method according to claim 7, wherein the solid cancer is colorectal cancer, lung cancer, breast cancer, pancreatic cancer, or gastric cancer.

19. The method according to claim 1, wherein the solid cancer is colorectal cancer.

20. The method according to claim 6, wherein 75 to 120 mg/m$^2$/day of irinotecan hydrochloride hydrate is administered.

* * * * *